United States Patent
Sköld

(10) Patent No.: US 6,674,829 B1
(45) Date of Patent: Jan. 6, 2004

(54) NEUTRON RADIATION INSTALLATION FOR TREATMENT OF CANCER

(75) Inventor: Kurt Sköld, Nyköping (SE)

(73) Assignees: Radicon AB, Stockholm (SE); Studsvik AB, Nykoping (SE)

(*) Notice: Subject to any disclaimer, the term of this patent is extended or adjusted under 35 U.S.C. 154(b) by 0 days.

(21) Appl. No.: 09/786,758

(22) PCT Filed: Sep. 8, 1999

(86) PCT No.: PCT/SE99/01564
§ 371 (c)(1),
(2), (4) Date: Mar. 9, 2001

(87) PCT Pub. No.: WO00/15298
PCT Pub. Date: Mar. 23, 2000

(30) Foreign Application Priority Data

Sep. 10, 1998 (SE) .............................................. 9803072

(51) Int. Cl.[7] ............................................. G21C 1/06
(52) U.S. Cl. ..................... 376/346; 376/159; 376/458; 376/906; 250/492.1; 250/503.1; 600/1
(58) Field of Search ................................ 376/346, 159, 376/458, 906; 250/492.1, 503.1; 600/1–8

(56) References Cited

U.S. PATENT DOCUMENTS

| 4,675,150 | A |   | 6/1987 | Russell ........................ 376/340 |
| 5,433,693 | A | * | 7/1995 | Ott ................................. 600/1 |
| 5,553,105 | A | * | 9/1996 | Xiao ............................ 376/159 |
| 5,703,918 | A | * | 12/1997 | Hiismaki et al. ........... 376/458 |
| 5,976,066 | A | * | 11/1999 | Yanch et al. ................... 600/1 |

OTHER PUBLICATIONS

Yanch et al, Accelerator–based epithermal neutron beams for neutron capture therapy, Advances in Neutron Capture Thearapy, 1993, p. 95–98.*

* cited by examiner

Primary Examiner—Michael J. Carone
Assistant Examiner—Jack Keith
(74) Attorney, Agent, or Firm—Larson & Taylor PLC

(57) ABSTRACT

A neutron radiation installation for treatment of different types of cancer tumours, comprising a source of neutrons (11), like a nuclear reactor or an accelerator dependent source of radiation, a conventional filter (14) for reducing the radiation energy to a suitable level for radiation treatment of cancer tumours, having low energetic neutron beams of an energy of between 1 eV and 40 keV, or preferably between 1 keV and 20 keV, and a radiation tube (22) out of which radiation beams are emitted towards a patient (10) having a cancer tumour (23), whereby an optimum radiation is obtained at a distance of between 50 and 100 cm from the output surface of the conventional filter (14), and in which the installation comprises an additional radiation filter (21) mounted between the conventional filter (14) and the output of the radiation tube, which additional filter is of a material which filters off neutrons in the epithermic spectrum from low energetic neutron beams up to an energy of about 1 keV, in particular metallic lithium, or another form of the element lithium, which has been enriched to about 95% in the isotope $Li^6$.

5 Claims, 4 Drawing Sheets

NEUTRON RADIATION INSTALLATION FOR TREATMENT OF CANCER

Figure 1:
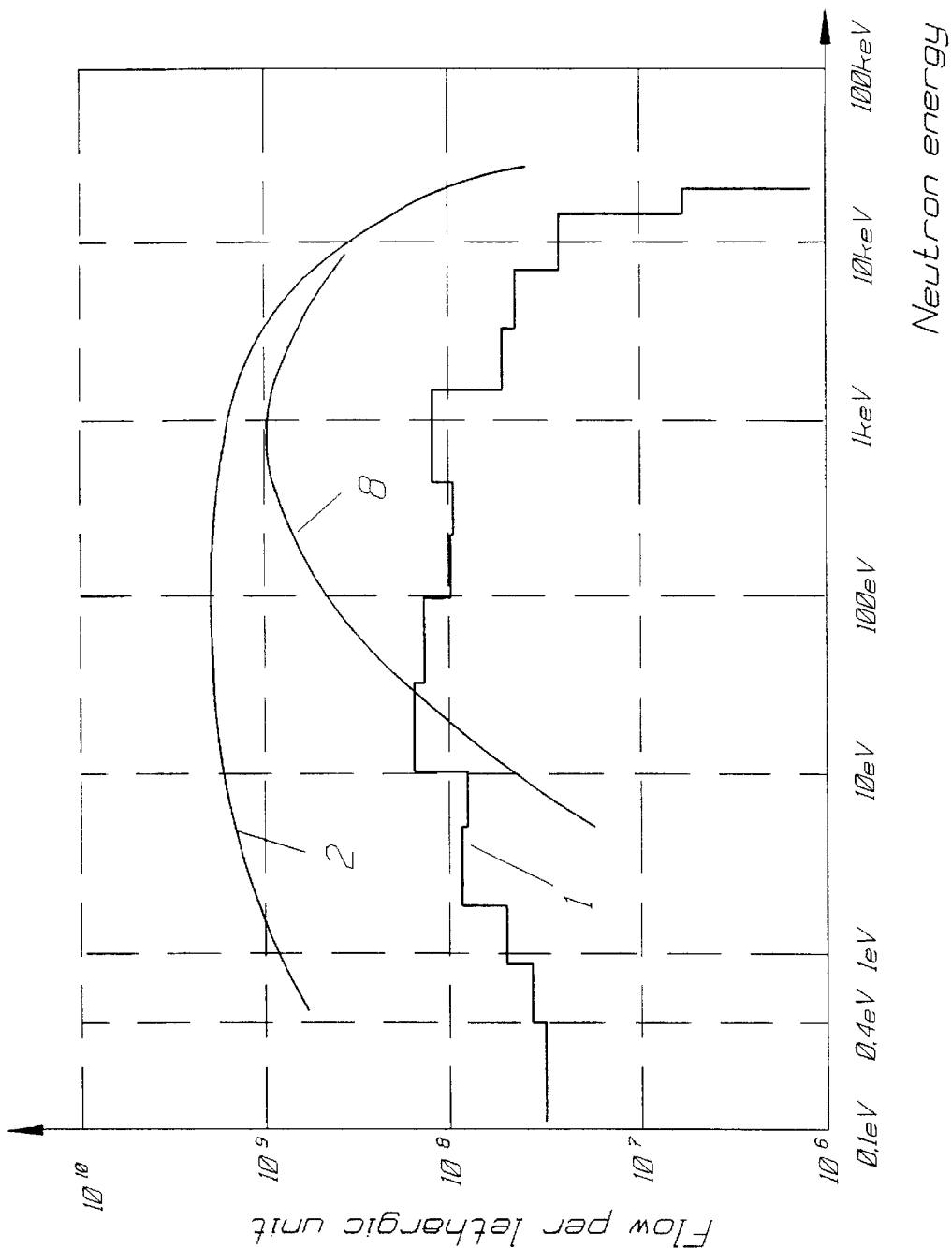

The present invention generally relates to a radiation apparatus or installation for treatment of various types of cancer tumours, and the invention is more particularly directed to a neutron radiation apparatus/installation for treatment of cancer and of the type which emits neutron beams having a neutron energy of up to 40 keV, and in which the source of neutrons is preferably a nuclear reactor formed with a filter providing a radiation field having preferred low energy neutrons by means of which the tumour is irradiated.

The invention has, in the first place, been developed as the solution of the problem of irradiating tumours in the brain of humans and animals, which tumours have so far been considered extremely difficult to treat. It is, however, obvious that the invention is as well useful for treatment of many other types of tumours and types of cancer.

During the development of the invention there has, in the first place, been used a nuclear set up at Studsvik, Sweden, in the following referred to as R2-0. This is, of course, no limitation of the invention, but many other types of similar reactors can as well be used, like also accelerator based neutron sources, in which the neutrons are produced for example by the known reaction $Li^7 (p, n) \rightarrow Be^7$, in which an accelerated beam of protons (p) is directed to a radiation target comprising the lithium isotope $Li^7$, whereby neutrons (n) are emitted resulting in the beryllium isotope $Be^7$ as the final product.

GENERAL

Shortly after the discovery of the neutron (1932) Locher suggested that neutron beams, in combination with isotopes having a high cross section (high probability) for absorption of neutrons, could be a method of radiation treatment of tumours. The nuclear process which has, in the first place, been discussed to this application is absorption of neutrons in the isotope boron-10

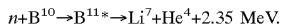

$$n + B^{10} \rightarrow B^{11*} \rightarrow Li^7 + He^4 + 2.35 \text{ MeV.}$$

A boron compound is introduced in the body, whereby the boron compound directs itself to cancer cells and is sucked into same and/or is positioned on the surface of the cancer cell. The reaction is that the $B^{10}$ core absorbs/captures a neutron and is transformed to $B^{11}$ which spontaneously is decomposed to the nuclear fragments $Li^7$ and $He^4$ having a combined kinetic energy of 2.35 MeV (million electron volt). The fragments are electrically charged and therefore strongly ionized along their paths in the surrounding material. The interaction with for instance biologic tissues is so effective that the fragments are completely braked to stop at a distance of 5–10 micrometer (millions of meter), which is the approximate dimension of a human cell. The energy in the molecular cell bond is of the magnitude of some few eV, and the fragments, having an energy of the magnitude of millions of electron volt breaks during its way through the cell millions of molecular bonds, and this is sufficient for destroying the reproductive ability of the cell. If the nuclear process is performed underneath the surface or in the core of a cancer cell the uncontrolled cell splitting is thereby stopped. If a sufficient number of cancer cells are accordingly inactivated the cancer is remedied.

The probability that a cancer cell is knocked out is a product of the probability that there is a $B^{10}$ core on or in the cell and the probability that said $B^{10}$ cord absorbs/captures a neutron is thereby transferred to $B^{11}$ and thereby sponta- neously becomes decomposed. The method is named BNCT method (Boron Neutron Capture Therapy). The effectiveness of said method is strongly restricted by the demand that the radiation is not allowed to introduce harmful dose concentrations on healthy tissues, what in turn puts demands both on the boron distribution in and on the tumour cells and the spreading of the neutron field and the energy distribution in the tumour and in healthy tissues.

The problem with deposition of boron or the boron compound in the cancer cell is a question raised in the biochemical research work, where extensive work is being made for providing effective target seeking substances. To-day there is a product on the market (named BPA) which is the amino acid phenylalanine which has been charged with boron atoms, which product issues an excess of boron in the tumour cells as compared with that of healthy tissues by a factor of about three. Other types of boron carrying substances can be used for the same purpose.

The second factor of importance for the therapeutic effect is the spreading of the neutron field in the tissue and the energy distribution of the neutrons in the tumour and in healthy tissues. Said questions belong to the neutron physical research field.

The energy distribution of the neutron beam is of decisive importance for the effect of the therapy in several respects. Firstly the probability that the neutrons are absorbed/captured in the $B^{10}$ core, that is the desired therapeutic effect, is strongly depending on the energy. The probability is inverse proportional to the speed "v" of the neutron (so called 1/V cross section) and is therefore a high probability for slow (low energy) neutrons. This means that there is a wish for a radiation field having low energy neutrons at the tumour. A complication is that the dose load on healthy tissues is also depending on the neutron energy. The low energetic components in the radiation field both leads to capture in $B^{10}$ in healthy tissues and also to capture in nitrogen and hydrogen cores in the tissues with a resulting non desired emission of reaction fragments and gamma radiation.

For deeply located tumours the situation is further more complicated in that a field of low energetic neutrons is quickly dampened during the passage thereof through the tissue, since this leads to a neutron intensity which is decreasing from the surface of the tissue with a relatively high dose load on the skin and intermediate healthy tissue. The principle method of improving the situation is to perform the radiation by means of neutrons which in the starting position has a relatively high energy. During the passage through the tissue the neutrons are braked by collision with atom nucleus in the tissue (in front of all hydrogen) so that a maximum of slow neutrons in thermal balance with the tissue (thermal neutrons) are built up 2–4 cm from the surface with a tail of low energy neutrons on further distances in the tissue.

Also this method is limited since too high neutron energies lead to a serious dose loads of other type. At a collision of a neutron with a hydrogen core a large part of neutron energy is transferred to the recoiling hydrogen core which, in turn, strongly ionizes (destroys) the tissue. The optimum compromise between said contradictory terms is to execute the radiation with neutrons in an intermediate area of the energy scale, namely by means of so called epithermic neutrons in the area between 1 eV and 40 keV, or preferably between 1 eV and about 20 keV. This can be done in that the neutrons which are produced in the reactor and which has energies in the MeV area are "filtered off" by means of a filter block comprising elements having appropriate neutron physical properties. In the filter there is obtained a selective spreading and retardation of the neutrons, and from the output of the filter there is obtained a radiation beam by neutrons which are relatively evenly distributed in the energy area of 1 eV–40 keV, or preferably 1 eV–20 keV.

This method represents the known technology on which BNCT installations in USA (Brookhaven and MIT) and in Finland (Otaniemi) are based.

BNCT INSTALLATION IN THE R2-0 REACTOR AT STUDSVIK-SWEDEN

The neutron physical requirements for a BNCT installation are far better at the R2-0 reactor than in any existing installation all around the world depending on the specific construction of the Studsvik reactor, which is diagrammatically shown in FIG. 3 and which is to be described in the following. The reason is that the reactor core in the Studsvik reactor R2-0, differing from many other reactors, lacks both a permanent reflector and a reactor tank. The core hangs freely in the reactor pool and an optimum configuration of filter material can be installed in a filter between the reactor core and the radiation position for the patient.

The diagram of FIG. 1 shows the intensity and the energy distribution of the neutron beam at the patient position in the installation in Finland (FIR1), curve and in the suggested and so far planned installation at Studsvik R2-0, curve 2. From the diagram is evident that the intensity of epithermic neutrons is ≈10 times higher in the R2-0, curve 2, than in the Finnish installation, curve 1. As will be discussed in the following also the energy distribution and other radiation parameters are slightly more favourable in R2-0 than in other installations.

Other radiation properties of importance for the therapy outcome are the direction distribution of the neutrons—neutrons in a parallel beam of rays gives an optimum radiation field in the tissue—and the level of gamma radiation from the reactor and from neutron capture processes in the radiation filter. A group at INEEL, Idaho Falls, USA, has built up a library of computer programs (PPS=Patient Planning Software) by means of which the therapy effect of BNCT beams having given physical parameters can be calculated. In the program the outcome of the radiation is calculated in the form of the factor "Tumour Control Probability" as a function of the dose load on healthy tissue, see FIG. 2. Considering the radiation parameters which have been discussed above it is also possible, by means of said program PPS, to generate the theoretically optimum radiation properties for treatment of tumours at different depths in the tissue, see "optimum curve 2" in FIG. 2. In the diagram the ideal beam for treatment of a brain tumour at the depth of 8 cm (most difficult case) is represented by the graph BNCT_1, curve 3. Other graphs in the diagram refer to the results for the corresponding cases for the most important BNCT beams which are at present available in the west world. The beams are represented according to the following:

| BMRR: | Brookhaven, USA | curve 4 |
|---|---|---|
| HFR: | Petten, The Netherlands | curve 5 |
| FIR1: | Otaniemi, Finland | curve 6 |

The outcome for the beam having a conventional filter which is planned to be used in the R2-0 reactor is represented by the graph marked by S544, curve. As evident from the diagram the beam at R2-0 can be expected to give a better treatment result than any of the other beams. This is obvious in that the curve shows that the radiation dose against healthy tissue is substantially less (curve is located further to the left) than from other installations, curves 4, 5 and 6.

INVENTION

During the last half-year an extraordinarily important further development of the neutron technology has been made for the R2-0 installation at Studsvik. The starting point for said development is the fact that the neutrons having low energies in the epithermic spectrum give, seen relatively, a worse contribution to therapy effect at a given dose load on healthy tissue.

Figure 4:
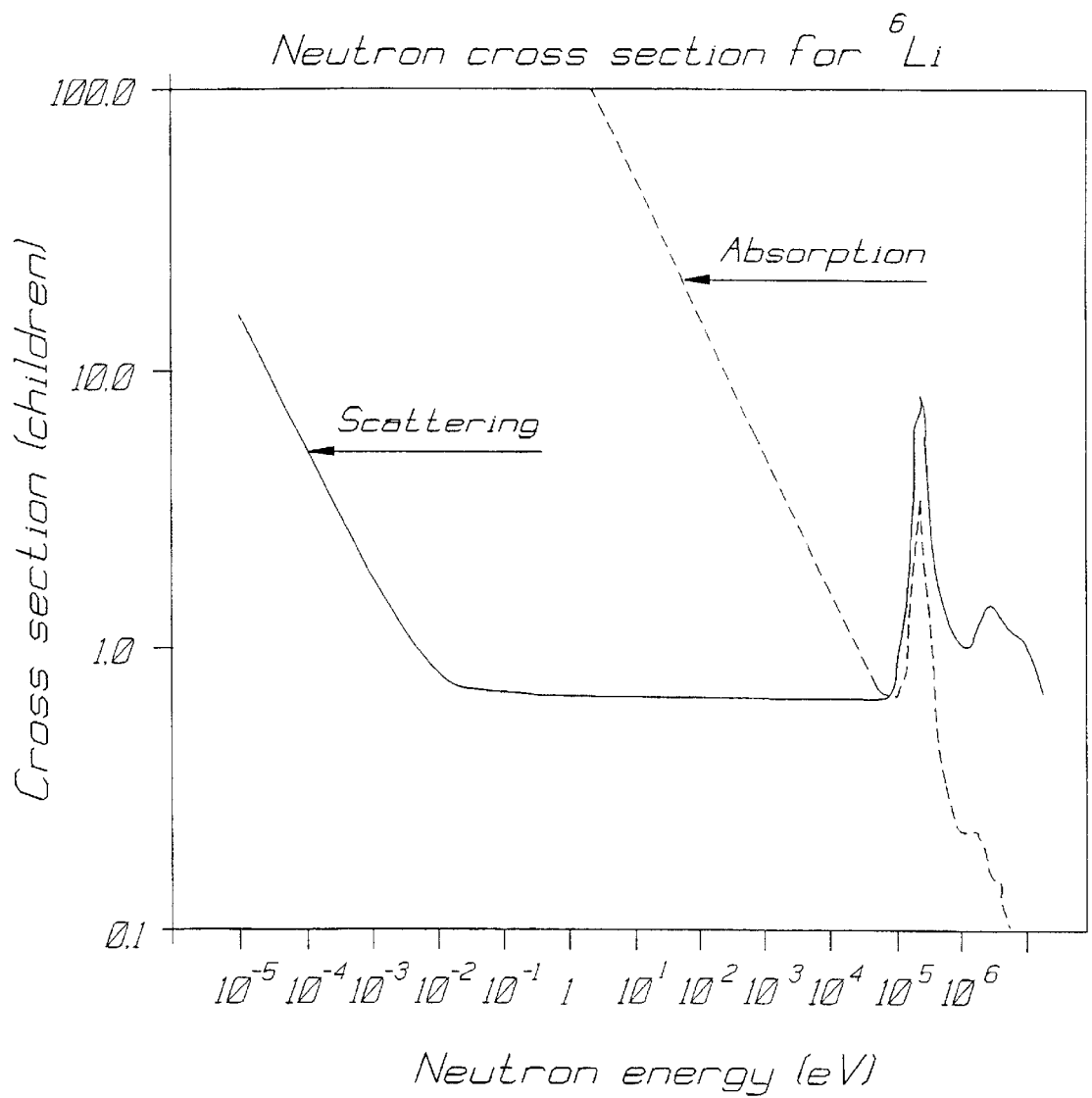

By filtering off neutrons up to a certain energy, the value of which is determined by depth on which the actual tumour is located, the outcome of the radiation thereby can be improved. The technical problem in providing this is to find a filter material which selectively removes, by spreading processes in the filter material, neutrons having a relatively low energy, up to energies in the area of some few keV, without too much damping, concurrently therewith, the intensity of neutrons having relatively higher energies which are necessary for the radiation treatment, or which too much affects the direction distribution in the therapy beam. An optimum choice for this purpose is a plate of metallic lithium, or another form of the element lithium which is enriched up to =95% in the isotope $Li^6$. In FIG. 4 is shown the neutron cross section for $Li^6$. From the figure is evident that the absorption/capture is high for low energies and thereafter decreases quickly when the energy is increases, and this makes it possible to filter off neutrons having low energies. From the figure is also evident that the spreading cross section is low for energies in the interesting energy area of 1 eV–40 keV. The peak of the cross section curves at =250 keV is another advantage since it contributes to dampen the intensity of neutrons at high energies which have passed the conventional filter.

Figure 2:
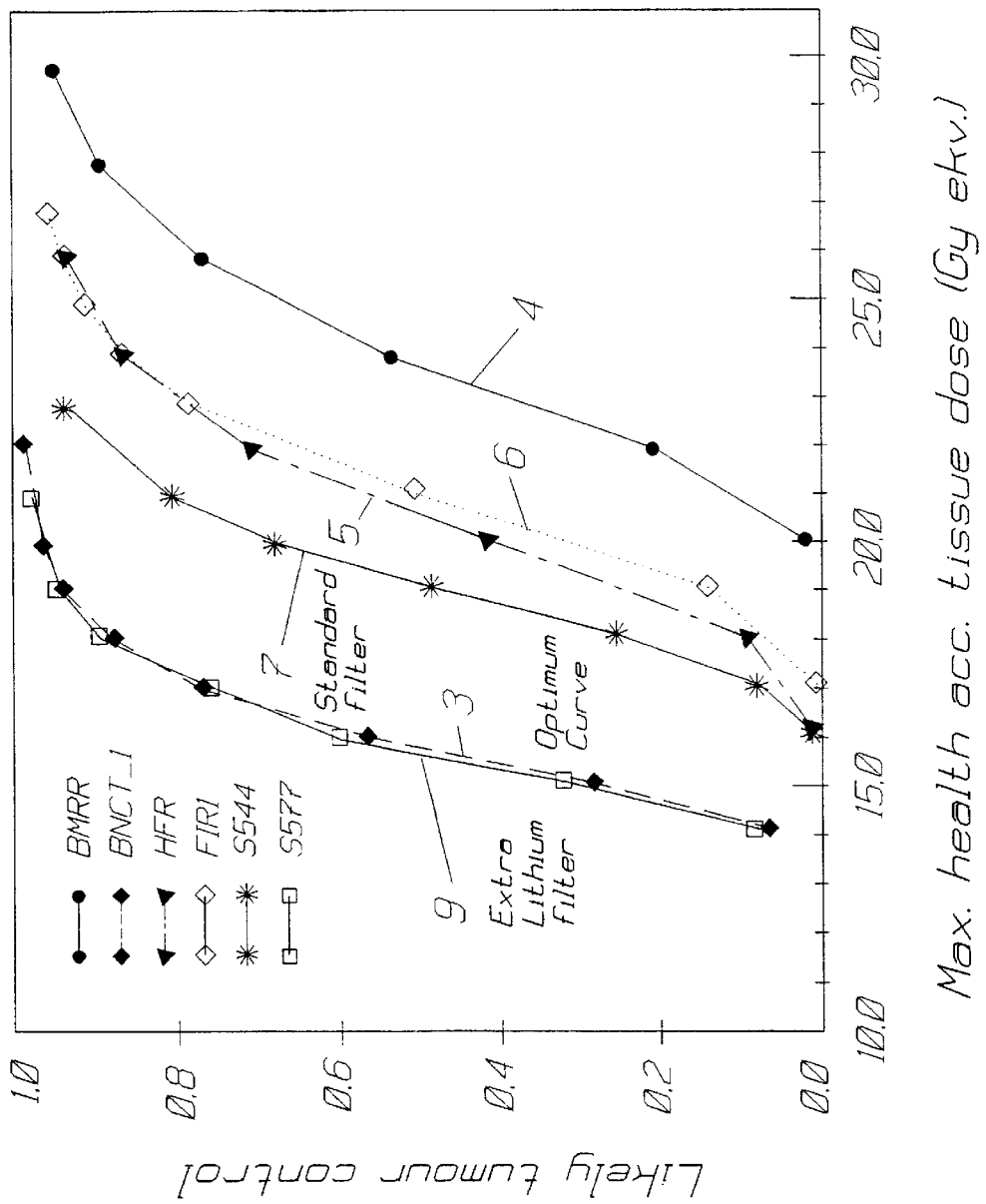

In the diagram of FIG. 1 is shown, by curve 8, the change of the energy distribution by an addition of a 2 cm thick Li filter mounted between the conventional standard filter of the reactor and the patient to be radiation treated. The graph having the designation S577, curve 9 of FIG. 2, shows that the R2-0 beam having said filter configuration is equivalent to the above mentioned ideal beam as hypothetically calculated. This is surprising and unique. For treatment of tumours at other depths than 8 cm the optimum result is obtained by varying the thickness of the Li filter.

DETAILED DESCRIPTION

The accompanying drawings illustrate the invention.

In FIG. 1 is shown a curve of the neutron energy in relation to the flow per lethargic unit.

FIG. 2 shows a group of curves from various radiation installations, which show a maximum dose (Gy equivalent) in healthy tissue in relation to a probable tumour control.

Figure 3:
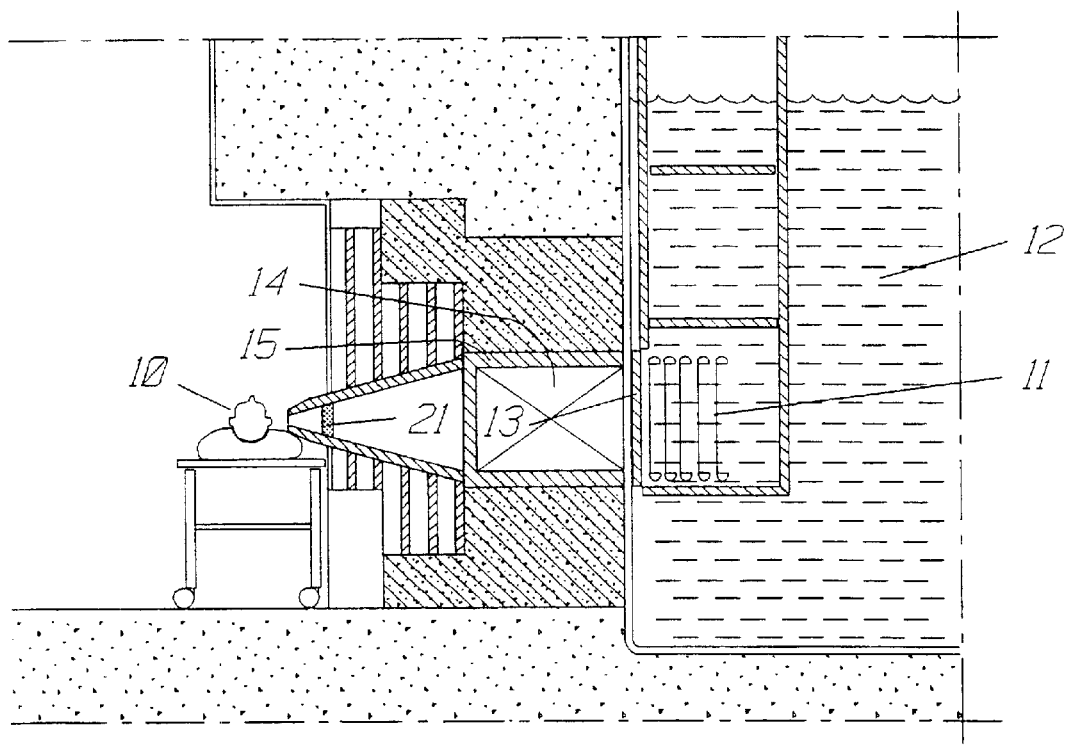

FIG. 3 diagrammatically shows a radiation installation according to the invention.

Figure 5:
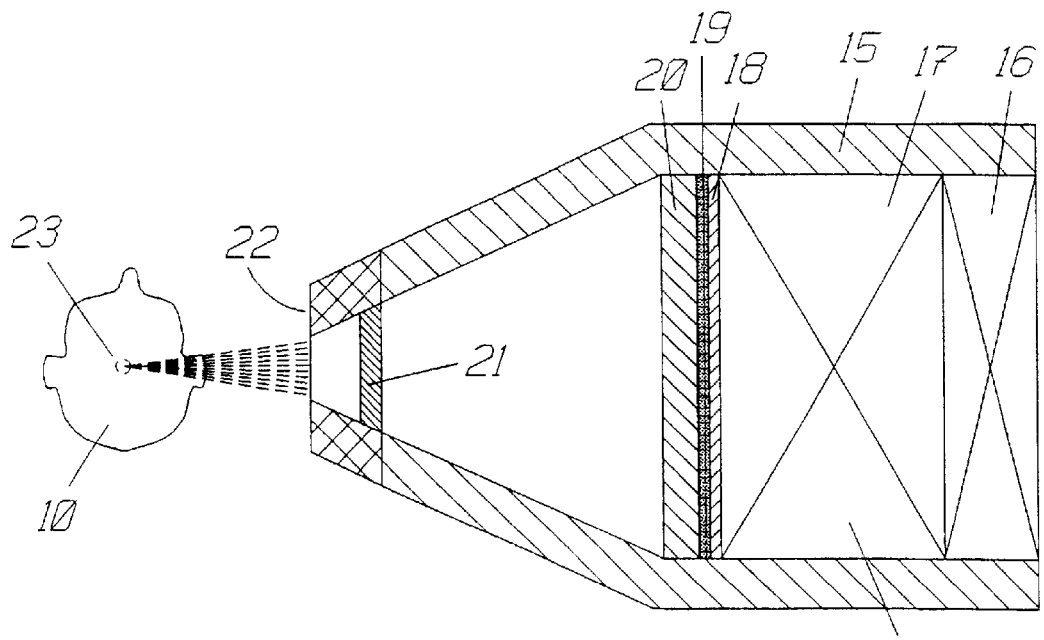

FIG. 4 shows the cross section (probability) for capture and spreading, respectively, of neutrons in $Li^6$ at various neutron energies, and FIG. 5 shows, more in detail, the very radiation feeding at the installation according to the invention shown in FIG. 3.

In FIG. 1 is thus shown a curve over the neutron energy in relation to the flow per lethargic unit both for a known installation curve 1, and for a Studsvik installation having a conventional radiation filter, curve 2, and for a radiation installation according to the invention, curve 8.

FIG. 2 shows a group of curves of maximum radiation dose in healthy tissue expressed in Gray Equivalent (Gy equivalent) in relation to probable tumour control or tumour decomposition. The ideal beam for treatment of a brain tumour at the depth of 8 cm (most difficult case) is thereby shown by the graph 3 having the designation BNCT_1 which is the optimum curve for radiation treatment of such a brain tumour, which curve 3 has been calculated by means of a computer as known per se. The graphs 4, 5 and 6 of the diagram relate to the results for corresponding cases for the most important of the BNCT beams which are available in the west world. The beams are designated according to the following:

| BMRR: | Brookhaven, USA | curve 4 |
|---|---|---|
| HFR: | Petten, The Netherlands | curve 5 |
| FIR1: | Otaniemi, Finland | curve 6 |

The outcome for the beam having a conventional filter in the R2-0 reactor at Studsvik is shown by the graph having the designation S544, curve 7. As evident from the diagram the beam at R2-0 can be expected to give a substantially better treatment result than any of the other beams, corresponding to the presently known technics for radiation treatment of brain tumours, what is observed in that the curve shows that the radiation dose against healthy tissue is substantially less (curve located to the left) than from known installations, curves 4, 5 and 6.

The curve 9, marked with S577, corresponds to a treatment in the reactor R2-0 in the case that the reactor is completed by an additional filter, by means of which neutrons are filtered off up to a certain energy the value of which is determined based on the depth at which the tumour is located, whereby consequently the outcome of the radiation can be improved. The technical problem of providing such improvement is to find a filter material which selectively removes neutrons having low energy, up to energies in the area of some few keV without concurrently therewith too much dampening, by spreading processes in the filter material, the intensity of neutrons at the higher energies which are required for the radiation treatment, or without too much affecting the direction spreading of the therapy beam. It is evident that the curve 9 nearly exactly coincides with the calculated optimum radiation curve 3. This is very surprising, and gives a great hope of future successful radiation of deeply located brain tumours, and hopefully healing of brain tumour cancer and also other types of tumours for which the BNCT method is not useful.

When treating tumours at less depths in the tissue the treatment result can be optimized in that the energy distribution zone is displaced from the distribution which is the optimum for deeply located tumours (1 keV–40 keV) to less energies. This can be provided in that the neutrons from the reactor are braked by means of a block comprising for instance Al and $D_2O$ having various thickness and chosen so that the intensity of neutrons are maximized in the energy area which is optimized for the treatment. For shallow tumours the thickness of the block is adapted so that a solely thermal energy distribution is obtained. For tumours at greater depth in the tissue the thickness of the $D_2O$ block is reduced so that the average energy of the neutrons is displaced towards the epithermic area. This method, however, has as an effect that the beam contains a tail of low energetic neutrons of down to thermal energies. This gives a non-desired dose load at and closely inside the surface. Said tail of low energetic beams can be eliminated by using the above mentioned $Li^6$ filter having a thickness which is adapted so that neutrons having the non-desired energies are eliminated from the beam.

The said additional filter has to fulfil several different demands for modifying the spectrum. Firstly the absorbing filter material must have such probability of capture and spreading that neutrons having an energy up to the desired keV area are effectively captured at the same time as the spreading of neutrons is minimized. Extensive spreading of neutrons affect the beam unfavourably and affects the direction of the beam. Further the filter must provide an absorption/capture process which is not accompanied by gamma radiation. It has shown that $Li^6$ fulfils said high demands on the filter material. It is further important that the original neutron beam has such intensity that the remaining beam, after having passed the additional filter has sufficient intensity for making a radiation possible within a reasonable period of time. In the above mentioned reactor R2-0 at Studsvik the epithermical (E>0.4 eV) neutron flow originally was $1.4\times10^{10}$ $n/cm^2/s$ at the patient position, and when mounting a lithium plate the neutron flow was $3.6\times10^9/cm^2/s$, which is a quite sufficient flow of radiation giving suitable treatment times. In this case the patient was placed at about 75 cm distance from the output surface of the conventional filter Al—$AlF_3$—Bi.

In FIG. 3 is diagrammatically, and in a vertical cross section, shown an installation for radiation treatment of a patient 10 having a deeply located brain tumour, for instance at a depth of 8 cm. In the illustrated case the neutron source is a nuclear reactor, in which the core 11 is mounted hanging in the pool 12, and in which the radiation first passes a lead jacket 13 and thereafter a conventional filter 14 which is most clearly shown in FIG. 5. Said conventional filter, which is likewise encapsulated in an about 10 cm thick lead jacket 15 comprises, as seen in the radiation direction, an aluminum plate 16, a relatively thick plate 17 of Al—$AlF_3$, a thin plate of titanium, a thin layer of cadmium and a plate 20 of bismuth. The plates can have the following approximate thickness, which, as mentioned previously, gives a neutron flow at the illustrated installation of $1.4\times10^{10} n/cm^2/s$ at a reactor effect of 1 MW:

| Al | 20 cm |
|---|---|
| Al—$AlF_3$ | 50 cm |
| Ti | 2 cm |
| Cd | 0.5 cm |
| Bi | 8 cm |
| that is, in total | 80.5 cm |

As discussed above it is not appropriate that the beam contains neutrons having very low energy. To this end there is used an additional filter 21 which is mounted between the conventional filter 14 and the output 22 of the radiation tube. Said additional filter 21also is useful for filtering off radiation having too low energy, for instance energies lower than about 1 keV. A specially useful material for said additional filter 21 has shown to be lithium which is enriched in the isotope $Li^6$.

The case illustrated in the drawing relates to radiation of a brain tumour 23 located at a depth of about 8 cm in the brain of a patient. In this case it has shown useful that the lithium filter has a thickness of about 2 cm considering the energy spectrum obtained and the depth of the tumour.

For treatment of tumours at other depths than 8 cm, like in the above related case, the thickness of the lithium filter is varied so that a relatively thin lithium filter is used for a more shallowly located tumour and a relatively thicker lithium filter is used for a more deeply located tumour.

In FIG. 4 is shown the neutron cross section for capture/absorption and for spreading of $Li^6$. From the figure is evident that the absorption is high for low neutron energies and is reduced to a neglectible value at some tenth keV. The spreading cross section is sufficiently low over the entire energy interval which is of interest for a BNCT beam. Both cross sections show a peak at ≈250 keV, the effect of which is to further improve the quality of the beam by filtering off harmful neutrons at high energies.

BNCE METHOD IN A HISTORICAL APPROACH

Clinical experiments with neutron radiation of glioblastoma patients were started in Brookhaven, USA in the year 1951. In the experiments there were used low energetic (thermal) neutrons and boron carrying substances having low selectivity for specific boron deposition/capture in the tumour. For reasons which are easy to understand to-day the results were not successful and the activity was ceased. At the end of the 1960th the experiments were resumed in Japan, now with better selectivity in the boron deposition, but still with beams of thermal neutrons. About 200 patients having glioblastoma have so far been treated. The reporting from the experiments in Japan have indicated a substantial improvement of the therapeutic effects as compared with the radiation therapy with photons which is a routine method all over the world.

The Petten group system having the above mentioned radiation designation HFR, also marked in FIG. 2, the Petten Group in the Netherlands, curve 5 of FIG. 2 has, for historical reasons, chosen another boron element (BSH), and there are reasons to expect that the results thereof will be only little successful. The installation in Finland now also is ready to be used, and the first patient radiation treatments are expected to take place during the year 1999. In the Finnish project it is intended to use BPA as the boron carrier.

CLINICAL SITUATION FOR GLIOMA TREATMENT

Glioma is the common name for those tumours which are formed by tumour transformation of the support cells of the brain, the so called glia cells. There is a series of types of glioma. The largest type of said types is also the most malignant, namely glioblastoma multiformae. The average surviving time for patients having glioblastoma is about nine months, and there is practically no hope that a patient is healed. The treatment which is used to-day is surgical treatment followed by convention radiation treatment and eventually also treatment with cytostatics.

The basic reason for the difficulty of treating glioblastoma is the fact that the tumour cells grow extremely infiltratively. When the tumour is shown for the first time at X-ray examination it can therefore be presupposed that tumour cells already have been spread in the larger part of the brain tissue, even if said cells are present in a very low concentration. This is the explanation for the fact, which has been observed since long, namely that it is quite impossible to heal gliastoma by surgical operation. It is true that radiation treatment has a greater influence on tumour cells than on normal brain cells, but the difference is too little for the radiation treatment to be healing, even if the entire brain should be radiation treated. The same arguments also are valid for cytostatics.

One of the difficulties in transferring active substances to the tumour cells is the fact that only some few substances pass the so called blood-brain barrier between the blood vessels and the brain tissue. At the type of BNCT which is used at Brookhaven boron atoms are coupled to the amino acid phenylaianine. Normally phenylalanine passes the blood-brain barrier and is also selectively captured by quickly growing cells. It seems that BPA has the same characteristics. Theoretically it is therefore reasonable to believe hat BPA can be enriched in all the tumour cells of the entire brain volume. The experiments which have been made are supporting said belief. Supposing that a suitable spectrum of neutrons can be obtained it seems that a neutron radiation from both sides of the head might generate a neutron flux in the brain tissue which flux is relatively uniform. An important factor for this development is the filter structure which has been invented according to the Studsvik project. At the survey of the present situation for BNCT at Lund, Sweden, in the summer 1999, it was considered that a radiation should be obtained in the tumour, by a "two beam" neutron radiation and BPA, corresponding to 30 Gy in a single dose radiation, whereas the radiation in normal brain tissue should be 10 Gy. In this connection it should be reminded that the radiation which is routinely used against metastasis has a lowest dose of 25 Gy. The combination of BPA+the theoretically optimum neutron radiation which can be provided at the Studsvik installation must be considered utterly promising. It is considered quite reasonably to count upon a clear improvement of the therapeutic effect. Further improvements thereafter can be obtained (if considered necessary) by chemical improvements of the carrier molecules.

| REFERENCE NUMERALS | | | |
|---|---|---|---|
| 1 | (curve) | 13 | lead jacket |
| 2 | (curve) | 14 | standard filter |
| 3 | (curve) | 15 | lead jacket |
| 4 | (curve) | 16 | Al |
| 5 | (curve) | 17 | Al—$AlF_3$ |
| 6 | (curve) | 18 | Ti |
| 7 | (curve) | 19 | Cd |
| 8 | (curve) | 20 | Bi |
| 9 | (curve) | 21 | additional filter |
| 10 | patient | 22 | output |
| 11 | source of neutrons | 23 | tumour |
| 12 | water pool | | |

What is claimed is:

1. Neutron radiation installation for treatment of different types of cancer tumors, comprising:
   a source of neutrons,
   a first filter for reducing a radiation energy of the source of neutrons to a level for radiation treatment of cancer tumors, the radiation energy reduced by said first filter producing low energetic neutron beams with an energy of between 1 eV and 40 keV,
   a radiation tube from which the neutron beams are emitted from an output towards a patient having a cancer tumor, and
   a second radiation filter mounted between the first filter and the output of the radiation tube, which second filter is a plate of metallic lithium, or another form of the element lithium, which has been enriched to about 95% in the isotope $Li^6$,
   has a thickness of about 2 cm over all of the output of the radiation tube directed to the patient, and filters off neutrons in the epithermal spectrum from the low energetic neutron beams up to an energy less than about 1 keV.

2. Neutron radiation installation according to claim 1, characterized in that the source of neutron beams is a nuclear reactor or an accelerator dependent source of neutrons.

3. Neutron radiation installation according to claim 1, characterized in that the second filter lets through beams having an energy of between 1 keV and 20 keV.

4. Neutron radiation installation according to claim 1, characterized in that the second filter is mounted succeeding the first filter and in advance of the radiation position zone.

5. Neutron radiation installation according to claim 1, characterized in that the installation is formed so that an optimum radiation effect is obtained at a distance of about 50–100 cm from the output surface of the filter.

* * * * *